(12) United States Patent
Curcie et al.

(10) Patent No.: US 6,660,042 B1
(45) Date of Patent: Dec. 9, 2003

(54) METHODS OF BIOMIMETIC FINGER CONTROL BY FILTERING OF DISTRIBUTED FORELIMIB PRESSURES

(75) Inventors: David J. Curcie, Toms River, NJ (US); James A. Flint, Williamstown, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/776,100

(22) Filed: Feb. 2, 2001

(51) Int. Cl.$^7$ .............................. A61F 2/48; A61F 2/70
(52) U.S. Cl. .............................. 623/24; 623/25; 623/64
(58) Field of Search .............................. 623/24, 25, 64

(56) References Cited

U.S. PATENT DOCUMENTS

| | | | | |
|---|---|---|---|---|
| 3,652,980 A | * | 3/1972 | Goupillaud | 340/15.5 |
| 3,820,168 A | * | 6/1974 | Horvath | 3/1.1 |
| 4,650,492 A | * | 3/1987 | Barkhordar et al. | 623/24 |
| 4,748,672 A | * | 5/1988 | Nevill, Jr. et al. | 382/1 |
| 4,770,662 A | * | 9/1988 | Giampapa | 623/24 |
| 4,858,124 A | * | 8/1989 | Lizzi et al. | 364/413.01 |
| 5,336,269 A | * | 8/1994 | Smits | 623/25 |
| 5,367,475 A | * | 11/1994 | White | 364/724.01 |
| 5,413,611 A | * | 5/1995 | Haslam, II et al. | 623/25 |
| 5,447,403 A | * | 9/1995 | Engler, Jr. | 414/4 |
| 5,480,454 A | * | 1/1996 | Bozeman, Jr. | 623/24 |
| 5,598,505 A | * | 1/1997 | Austin et al. | 395/2.35 |
| 6,321,195 B1 | * | 11/2001 | Lee et al. | 704/241 |
| 6,416,480 B1 | * | 7/2002 | Nenov | 600/557 |

OTHER PUBLICATIONS

Abboudi, et al., "A Biomimetic Controller for a Multifinger Prosthesis," IEEE Trans. Rehab. Eng., vol. 7, No. 2, pp. 121–128, 1999.

Atal, "Automatic Recognition of Speakers From Their Voices," Proc. IEEE, vol. 64, No. 4, pp. 460–475, 1976.

Chang, et al., "Real–Time Implementation of Electromyogram Pattern Recognition as a Control Command of Man-Machine Interface," Med. Eng. Phys., vol. 18, No. 7, pp. 529–537, 1996.

Curcie, et al., "Biomimetic Finger Control by Filtering of Distributed Forelimb Pressures," IEEE Transactions on Neural Systems and Rehabilitation Engineering, vol. 9, No. 1, pp. 69–74, Mar. 2001.

Curcie, et al., "Recognition of Individual Heart Rate Patterns With Cepstral Vectors," Biological Cybernetics, vol. 77, pp. 103–109, 1997.

Kang, et al., "The Application of Cepstral Coefficients and Maximum Likelihood Method in EMG Pattern Recognition," IEEE Trans. Biomed. Eng., vol. 42, No. 8, pp. 777–784, 1995.

Kenney, et al., "Dimensional Change in Muscle as a Control Signal for Powered Upper Limb Prosthesis: A Pilot Study," Med. Eng. & Phys., vol. 21, pp. 589–597, 1997.

Kuo, et al., "Dual–Channel Audio Equalization and Cross–Talk Cancellation for 3–D Sound Reproduction," IEEE Trans. Consumer Electronics, vol. 43, No. 4, 1189–1196, 1997.

(List continued on next page.)

Primary Examiner—Bruce Snow
Assistant Examiner—Cheryl Miller
(74) Attorney, Agent, or Firm—Wolff & Samson PC

(57) ABSTRACT

A method for controlling digit movement of a prosthesis based on residual forelimb volitional pressures is provided. A filter is provided for discriminating from the distributed pressures to provide reliable digit control. The extracted commands can be used to control actuators in a hand prosthesis to restore biomimetic finger control to the user. Feature extraction algorithms can be based on signal amplitudes (peak amplitude or root mean square). Training signal validation can be based on cepstral encoding. The filter is trained under user supervision.

12 Claims, 6 Drawing Sheets

OTHER PUBLICATIONS

Lucaccini, et al., "The French Electric Hand: Some Observations and Conclusions," Bulletin of Prosthetics Research, vol. 10, No. 6, pp. 31–51, 1996.

Phillips, et al., "A Smart Interface for a Biomimetic Upper Limb Prosthesis," Proc. 6th World Biomaterials Congr., May 2000.

Shen, et al., "Filter–Based Coded Excitation System for High–Speed Ultrasonic Imaging," IEEE Trans. Med. Img., vol. 17, No. 6, pp. 923–933, 1998.

Strang, "The Singular Value Decomposition and the Pseudoinverse," Linear Algebra and its Applications, Forth Worth, TX: Harcourt Brace Jovanoch Publishing, pp. 443–451, 1998.

Vuskovic, et al., "Blind Separation of Surface EMG Signals," 18th Ann. Intl. Conf. of the IEEE Med. Biol. Soc., pp. 1478–1783, 1996.

* cited by examiner

INTENDED VOLITION

INPUT
CHANNEL

OUTPUT

MEASURED VOLITION $Y(i)_f$

METHODS OF BIOMIMETIC FINGER CONTROL BY FILTERING OF DISTRIBUTED FORELIMB PRESSURES

BACKGROUND OF THE INVENTION

1. Field of the Invention

This invention generally relates to methods for moving individual fingers on a prosthetic hand based on volitional pressures within the residual forelimb, and more particularly to a method of extracting individual finger commands from volitional forelimb pressures utilizing training and extraction algorithms based on signal amplitudes.

2. Related Art

Many upper limb amputees can readily learn to control a prosthetic hand by flexing and extending their residual forearm muscles. Their dexterity, however, is limited by current myoelectric technology to simple grasping, with one degree of freedom (DOF). Advanced electromyographic (EMG) processing methods may allow enhanced grasping control Okuno, et al., "Development of Biomimetic Prosthetic Hand Controlled by Electromyogram," Int. Workshop on Advanced Motion Control, Vol. 1, pp. 103–108, 1996; Vuskovic, et al., "Blind Separation of Surface EMG Signals," 18th Ann. Intl. Conf. of the IEEE Med. Biol. Soc., pp. 1478–1483, 1996, but remain limited for more dexterous motions due to the inherent noisiness and complexity of EMG signals. Alternatives to EMG-based control use muscle and tendon forces generated within the prosthetic socket. An early demonstration of this method was the French Electric Hand, which used pneumatic pressure generated voluntarily within the socket to actuate a 1-DOF hand. Lucaccini, et al., "The French Electric Hand: Some Observations and Conclusions," *Bulletin of Prosthetics Research*, vol. 10, no. 6, pp. 31–51, 1966.

Recently, Abboudi, et al., "A Biomimetic Controller for Multifinger Prosthesis," IEEE Trans. Rehab. Eng., Vol. 7, No. 2, pp. 121–129, 1999, showed that many amputees could express control over their extrinsic finger muscles through dynamic pressure and shape changes in their residua. These three-dimensional mechanical dynamics can be measured with myo-pneumatic (M-P) sensors within the socket. Phillips, et al., "A Smart Interface for a Biomimetic Upper Limb Prosthesis," Proc. 6th World Biomaterials Congr., May, 2000. A fine degree of residual limb muscle control was also demonstrated by amputees in a study using Hall effect magnetic movement sensors. Kenney, et al., "Dimensional Change In Muscle As a Control Signal for Powered Upper Limb Prostheses: A Pilot Study," Med. Eng. & Phys., vol. 21, pp. 589–597, 1999.

Previous studies have proposed methods to control prosthetic upper limbs based on EMG signals from one or more sites on the upper body. Kang, et al., "The Application of Cepstral Coefficients and Maximum Likelihood Method in EMG Pattern Recognition," IEEE Trans. Biomed. Eng., Vol. 42, No. 8, pp. 777–784, 1995; Park, et al., "EMG Pattern Recognition Based on Artificial Intelligence Techniques," IEEE Trans. Rehab. Eng., Vol. 6, No. 4, pp. 400–405, 1998; Chang, et al., "Real-Time Implementation of Electromyogram Pattern Recognition as a Control Command of Man-Machine Interface," Med. Eng. Phys., Vol. 18, No. 7, pp. 529–537, 1996; and Gallant, et al., "Feature-Based Classification of Myoelectric Signals Using Artificial Neural Networks," Med. Biol. Eng. Comput., Vol. 36, pp. 485–489, 1998. These methods can give the user control over basic limb movements such as elbow flexion, and wrist pronation. Decoding spatially distributed EMG signals is relatively difficult, however, requiring an initial pattern extraction from each EMG site, followed by a second extraction of the coupled patterns. Decoding of individual finger extensor EMG signals has been attempted, and may provide enhanced grasping control Vuskovic, et al. EMG signals, however, are inherently more complex than mechanical signals, and remain subject to problems such as relative motion between the skin and electrode, skin moisture, electrode corrosion, and noise.

Accordingly, what is needed, but has not heretofore been provided, is a method for sensing distributed mechanical forces in a limb corresponding to digit movement, and discriminating to provide reliable digit control. Herein, a pressure vector decoder (PVD) is developed that extracts multiple DOF from distributed pressures in the residual forelimb. The extracted commands can control fingers in real time, thus restoring a degree of biomimetic dexterity to the user.

The present invention relates to a user-trained filter for decoding volitional commands acquired from pressure sensors on a residual limb. The method is biomimetic, since the user controls the movement of mechanical fingers by activating appropriate finger flexor muscles. Pseudoinverse filtering has not been previously applied to biomechanical signals, but has been used for image processing and audio source separation. Cepstral analysis has been successfully used for pattern recognition applications in speech, EMG signals, and heart rate variability, knee vibrations, and arterial pulse velocity measurements.

OBJECTS AND SUMMARY OF THE INVENTION

It is a primary object of the present invention to provide a filter for extracting individual finger commands from volitional pressures within the residual forelimb.

It is an additional object of the present invention to discriminate individual finger commands from distributed pressures in the residual forelimb for controlling digit movement on a prosthesis.

It is even an additional object of the present invention to provide a method which utilizes linear filter parameters using the pseudoinverse of a feature matrix obtained from the forelimb signals, for extracting finger commands from volitional pressures within the residual forelimb.

It is a further object of the present invention to provide a method for controlling digit movement for a prosthesis wherein the prosthesis is trained under user supervision.

It is an additional object of the present invention wherein the feature extraction algorithm used in the present invention is based on signal amplitudes, derived from mechanical activity within the subject's anatomy.

It is an additional object of the present invention wherein the signal validation algorithm used in the present invention is based on cepstral encoding.

The present invention relates to filters for extracting finger commands from volitional pressures within the residual forelimb. The filters discriminate from the distributed pressures to provide reliable digit control. Linear filter parameters are trained using the pseudoinverse of the feature matrix obtained from the forelimb signals. Feature extraction algorithms are based on signal amplitudes (peak amplitude or root mean square). Cepstral distance analysis can be performed as a quality validation step for the training data, but is not necessary for the pseudoinverse filter method to work. Results with an amputee showed that multiple finger commands could be decoded reliably, representing real-time individual control over three prosthetic fingers. The filter is a critical component for biomimetic control and enhanced dexterity.

BRIEF DESCRIPTION OF THE DRAWINGS

Other important objects and features of the invention will be apparent from the following Detailed Description of the Invention taken in connection with the accompanying drawings in which:

FIG. 5A shows intended volition. The test set was two taps on each of three fingers, sequentially, sampled on 8 channels. FIG. 5B shows test input data. Shown are 12.5 seconds of data at a sampling rate of 200 Hz. Axes are the same as FIG. 4. Note: amplitude scale varies among channels, and differs from FIG. 4. FIG. 5C shows output signal response matrix. Traces represent 12.5 seconds of data, calculated from (1), including squaring and half-wave rectification. Rows represent the finger control output, and columns represent the intended volitional command.

DETAILED DESCRIPTION OF THE INVENTION

The present invention relates to a method for controlling digit movement of a prosthesis based on residual forelimb volitional pressures. The present invention includes a filter for discriminating individual finger commands from the distributed forelimb pressures to provide reliable digit control. The extracted commands can be used to control actuators in a hand prosthesis to restore biomimetic finger control to the user. Feature extraction algorithms can be based on signal amplitudes (peak amplitude or root mean square). Cepstral distance analysis can be performed as a quality validation step for the training data, but is not necessary for the pseudoinverse filter method to work. The filter is trained under user supervision.

Figure 1:
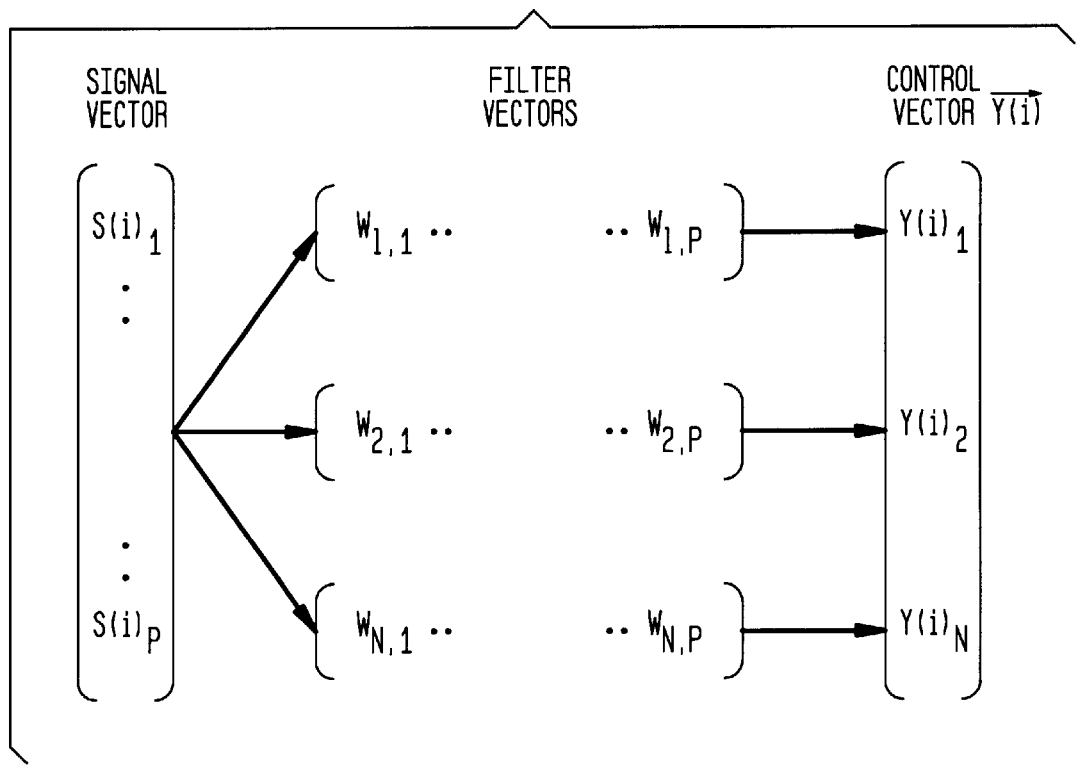
FIG. 1 is a diagram of discriminatory filtering of distributed interfacial pressure data. Filtering for three fingers is shown. Filter vectors $\vec{w}_f$ (f=1 ... N), comprised of custom weights, are applied to the signal vector, $\vec{s(i)}$, to obtain a control vector, $\vec{Y(i)}$, an approximation of the intended movement.

As shown in FIG. 1, Decoding finger commands from a spatial array of P pressure sensors involves filtering the input pressure vector, $\vec{s(i)}$, to obtain a real-time output, $\vec{Y(i)}$, for each of N fingers (f=1 ... N). $Y(i)_f$ is calculated as the linear combination of instantaneous pressure vector $\vec{s(i)}$ and a filter vector, $\vec{W}_f$, as follows:

$$Y(i)_f = |\vec{s}_i \vec{w}_f|^2 = \left| \sum_{k=1}^{P} (s(i)_k \cdot w_{f,k}) \right|^2 \quad (1)$$

Since only positive output is used for finger control, signals may be half wave recified (absolute value) and squared, as indicated in equation (1) above. FIG. 1 relates a specific set of input pressure vectors to a corresponding set of output vectors, $\vec{Y(i)}$, representing joint positions. Since the filter is trained by discrete movements, i.e. single finger flexions, its output relates only to those movements, and is not necessarily proportional to their intensities. Decoding of specific movement requests therefore may involve discretization of $Y(i)_f$ with an appropriate threshold function. In the ideal case, a simple amplitude threshold for $Y(i)_f$ should decode all movement requests with complete specificity.

Figure 2:
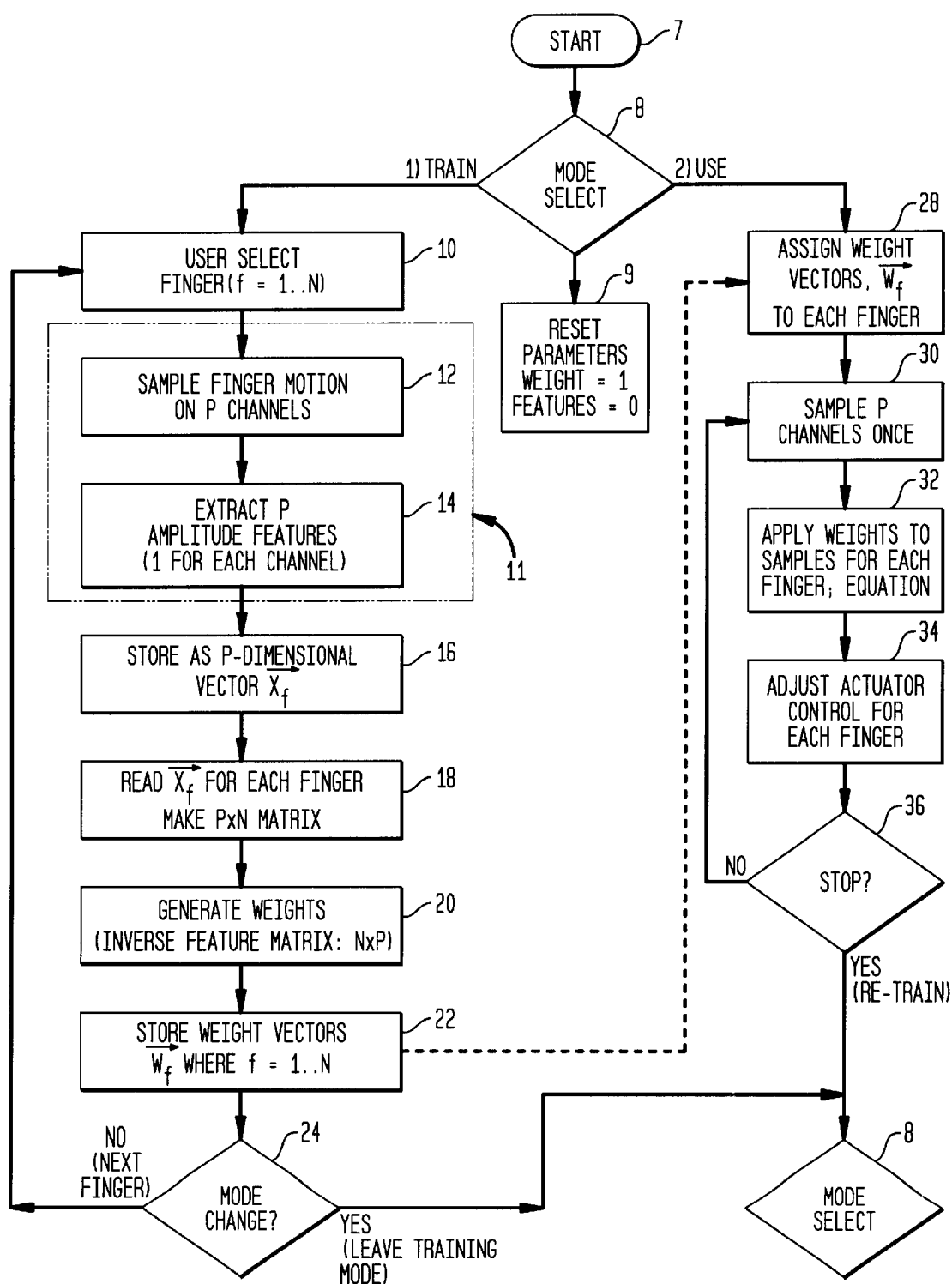
FIG. 2 is a flow diagram of hand and training and control. The system has two main modes: train and use, switchable from the user interface.

To optimize individual finger control, $\vec{w}_f$ for each finger is adapted for the user in a supervised training stage, as shown in FIG. 2 (left branch). Training the filter involves quantifying the degradation of the volitional commands through the limb and M-P sensor interface. It starts at 7 and the mode is selected at 8 wherein a training mode or using mode can be selected. Parameters can be reset at 9. If the user selects training mode in step 8, the user then selects a finger to train at 10. The finger motion is sampled on channels at 12. P amplitude features are extracted for each channel at 14, and stored as P-dimensional vector $\vec{X}_f$ at 16. The P-dimensional vector $\vec{X}_f$ is read for each finger and a P×N matrix is formed at 18. Weights are generated through inverse feature matrix N×P at 20. Weight vectors $\vec{w}_f$ are stored in 22, wheref=1 ... N. Thereafter, a mode change at 24 is determined, whereby the training mode can be left and a new mode selected at 8. For additional figures, there is no mode change and the training process is repeated.

Figure 3:
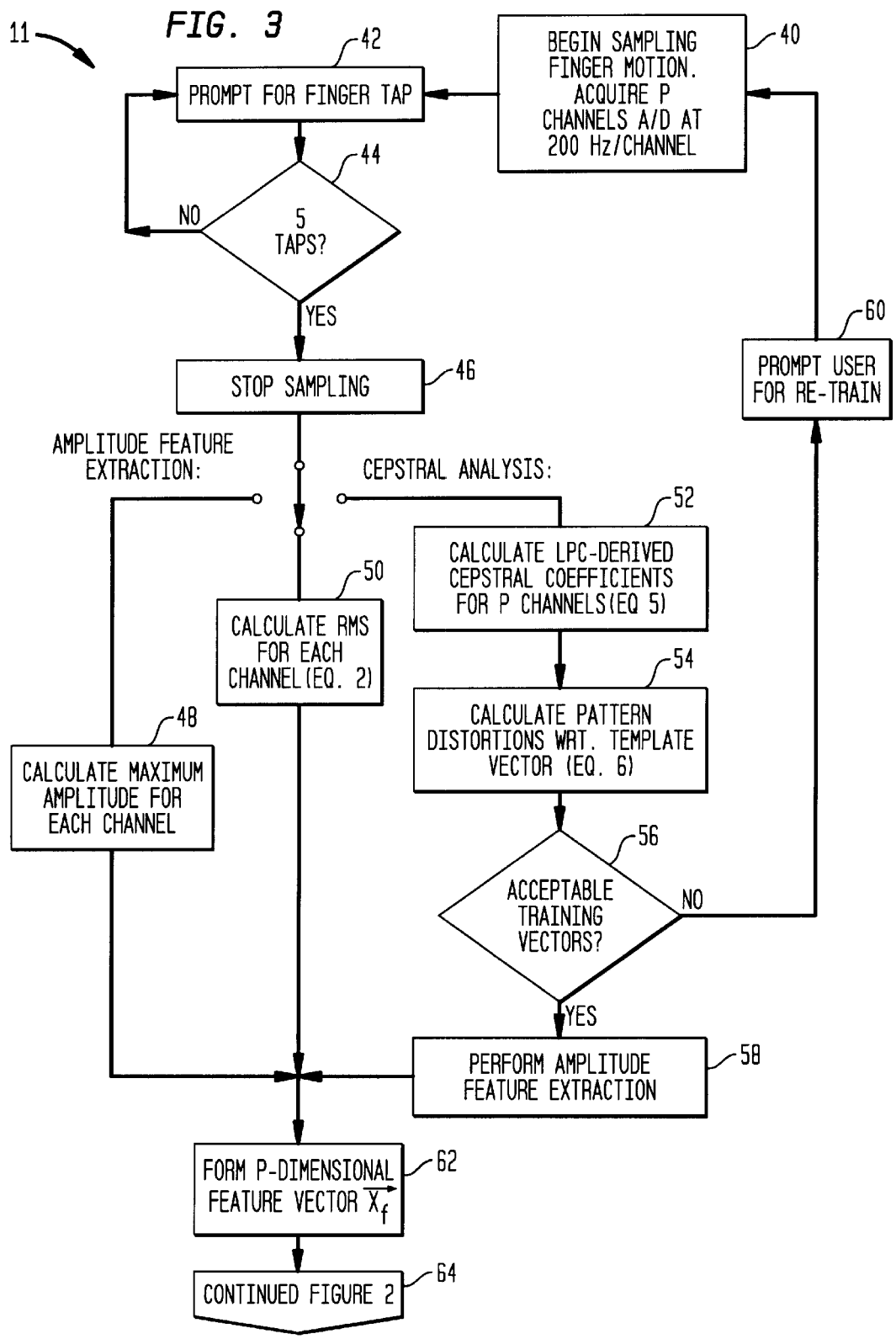
FIG. 3 is a flow diagram of training motion acquisition and feature extraction (expanded from FIG. 2). Motion acquisition is interactive. Two methods of feature extraction (peak amplitude or RMS), and cepstral signal analysis are shown.

Referring to FIG. 3, which shows a detailed view of block 11 in FIG. 2, sampling of finger motion begins at block 40 to acquire P channels A/D at 200 Hz/channel. The user is then prompted for a finger tap at 42. Once the user begins finger tapping, step 44 counts the total number of taps provided. When 5 taps are counted by step 44, tap sampling then stops at step 46. Extracting the amplitude features can be accomplished in a number of ways, for example, at 48 the maximum amplitude for each channel can be calculated. Alternatively, at 50, the RMS for each channel can be calculated in accordance with equation 2.

Alternatively, cepstral analysis can be utilized wherein the LPC-derived cepstral coefficients for P channels are calculated using equation 5 at 52. Pattern distortions can then be calculated using equation 6 at 54. At 56 if there are acceptable training vectors, amplitude feature extraction can be performed at 58. If there are no acceptable training vectors, the user can be prompted for re-training at 60, wherein block 11 is then re-iterated beginning at step 40. If acceptable training vectors are determined at step 56 and amplitude extraction performed in step 58, control is then given to step 62. At 62, P-dimensional feature vector $\vec{x}_f$ is formed based on either the maximum amplitude for each channel calculated in 48, the RMS for each channel calculated in 50, or after the amplitude feature extraction is performed in step 58. Thereafter, block 11 terminates, and the process of FIG. 2 is continued.

In summary, for training, a single amplitude feature is estimated for each channel during requested finger motions, forming a feature vector, $\vec{X}_f$. The simplest methods for feature extraction are based on signal amplitudes during specified movements, either absolute peak or root-mean-square (RMS). The peak amplitude method simply determines the largest absolute signal deviation from the baseline. The amplitude feature represents the impulse response of a finger-tap volition, measured by the M-P sensors. An effective feature for M-P signals is the RMS amplitude of a signal sequence during repeated specified movements (below). More complete signal features can also be used.

Equation (2) represents the RMS calculation performed for each channel in step 50 of FIG. 3.

$$\psi_k = \sqrt{\frac{1}{n}\sum_{i=0}^{n-1} s(i)_k^2} \tag{2}$$

The feature vectors for each finger, $\vec{X}_f$ (f=1 ... N), form the columns of a P×N feature matrix:

$$H = \begin{vmatrix} x_{1,1} & x_{1,2} & \cdots & x_{1,N} \\ x_{2,1} & x_{2,2} & \cdots & x_{2,N} \\ \vdots & & & M \\ x_{P,1} & x_{P,2} & \cdots & x_{P,N} \end{vmatrix} \tag{3}$$

H represents the degradation of the intended volitional commands through the residual limb and sensor interface. Its inverse restores the command impulses for the measured feature model, based on an algebraic restoration method Gonzalez, el al., "Image Restoration," Digital Image Processing, Reading Mass: Addison-Wesley Publishing Co., pp. 183–208, 1979; and Hendler, et al., "Deconvolutions Based on Singular Value Decomposition and the Pseudoinverse: A Guide for Beginners," J. Biochem. & Biophys. Meth., Vol. 28, No. 1, pp. 1–33, 1994. The filter, W, is the N×P discrimination matrix:

$$W = H^{-1} = \begin{vmatrix} w_{1,1} & w_{1,2} & \cdots & w_{1,P} \\ w_{2,1} & w_{2,2} & \cdots & w_{2,P} \\ \vdots & & & M \\ w_{N,1} & w_{N,2} & \cdots & w_{N,P} \end{vmatrix} \tag{4}$$

If H is not square, its pseudoinverse is calculated using singular value decomposition Hendler, et al.; and Strang, "The Singular Value Decomposition and the Pseudoinverse," Linear Algebra and its Applications, Fort Worth, Tex.: Harcourt Brace Jovanoch Publishing, pp. 443–451, 1988. Each of the N rows of W is a filter (weighting) vector, $\vec{w}_f$, representing the relative contribution of each input channel to the respective output channelf, as in equation (1).

The described filter may be applied to prosthetic finger control as shown in FIG. 2 (right branch). Referring to FIG. 2, if use mode is selected by the user, weight vectors $\vec{w}_f$ are assigned to each finger at 28. Then, P channels are sampled once at 30. Weights are applied to samples for each figure pursuant to an equation at 32. The actuator control for each finger is adjusted at 34. Thereafter at 36 if the user decides not to stop, P channels are sampled again at 30. If the user decides to stop in step 36, control is given back to mode selection step 8, whereby the user can then continue re-training.

Cepstral encoding is a method of representing the pattern of the training signal. It is therefore useful in determining the validity of the training sequences, or whether the training sequence was performed correctly by the user. Linear prediction-derived cepstral (LPC) vectors represent the TAP signal patterns, and selected cepstral coefficients represent training features. A set of p linear predictor coefficients, calculated via the Burg algorithm Press, et al., "Fourier and Spectral Applications, Linear Prediction and Linear Predictive Coding," Numerical Recipes in C, Cambridge, Mass: Cambridge University Press, pp. 564–572, 1992, can be converted to a set of LPC coefficients, $\{c_m\}_{m=1\ldots p}$, comprising a cepstral vector, c, using the recursive relationship, which have been discussed by Atal, "Automatic Recognition of Speakers From Their Voices," Proc. IEEE, Vol. 64, No. 4, pp. 460–475, 1976; Rabiner, et al., "Linear Predictive Coding Model for Speech Recognition," Fundamentals of Speech Recognition, A. V. Oppenheim, Ed., Englewood Cliffs, N.J.: Prentice-Hall, pp. 100–118, 1993; and Curcie, et al., "Recognition of Individual Heart Rate Patterns With Cepstral Vecotrs," Biological Cybernetics, Vol. 77, pp. 103–109, 1997; as follows:

$$c_m = -a_m - \sum_{k=1}^{m-1} (1 - k/m) \cdot a_k c_{m-k} \tag{5}$$

where $a_k$, $a_m$ are LP coefficients $c_m = m^{th}$ cepstral coefficient of the set $\vec{c}$ To evaluate the quality of the training data, the cepstral vector for any channel obtained during training is then compared to a template standard vector. To compare two cepstral vectors, $\vec{c}$ and $\vec{c}'$, of p dimension, the Euclidean ($L_2$) distance between them is calculated as Soong, et al., "On the Use of Instantaneous and Transitional Spectral Information in Speaker Recognition," ICASSP, Vol. 36, pp. 871, 1988:

$$D(\vec{c}, \vec{c}') = (\vec{c} - \vec{c}')^T (\vec{c} - \vec{c}') = \sum_{m=1}^{p} (c_m - c'_m)^2 \tag{6}$$

Pre-selected template standard vectors represent the desired movement pattern, such as a well-defined five-tap sequence. Insufficient proximity to the appropriate template vector, determined by a threshold for D, warrants a repeat acquisition of the training sequence by the user. Upon acceptance, a feature vector is formed from the features of P channels, using either of the peak amplitude or RMS feature extraction methods.

EXAMPLE

A. Data Acquisition

Results are presented from a 28-year old male amputee, of 10 years duration, with a 4-inch residuum (subject A). A second below-elbow amputee male subject (B) was also tested, who is 70 years of age, and received the injury approximately 50 years prior. Both subjects were tested following informed written consent, after approval of the study from the University Institutional Review Board. The subjects were able to perceive and attain motion control over 3 phantom fingers. This observation provided rationale for selecting a 3-finger control filter. Eight locations for sensor placement were determined by palpating the forearm during volitional finger motions, as described in Abboudi et al. A silicone sleeve custom fit for the subject was constructed, incorporating the M-P sensors into its structure at the chosen location. A custom socket was then placed over the sleeve, tightly enclosing the limb and sensors. Six of the 8 sensors were clustered around the flexor digitorum superficialis and the flexor carpi ulnaris, circumscribing a relatively small area of 28 cm$^2$.

Eight M-P sensors were connected via tubing to eight pressure transducers (Sensym SCX-01, Santa Clara, Calif.), connected to an 8-channel data acquisition board (DAP/1200, Microstar Laboratories, Inc., Bellevue, Wash.). Data from the M-P sensors were and sampled at 200 Hz per channel and 12-bits resolution, and stored to files for off-line processing.

The training and control system was emulated on a PC using LabVIEW graphical programming software (National Instruments Corp, Austin), and DADiSP signal processing software (DSP Development Corp, Cambridge). Data were exchanged between the two applications in real-time using dynamic data exchange (DDE). For the emulation, all sensor data were recorded off-line and read into the system.

B. Protocol

Figure 4:
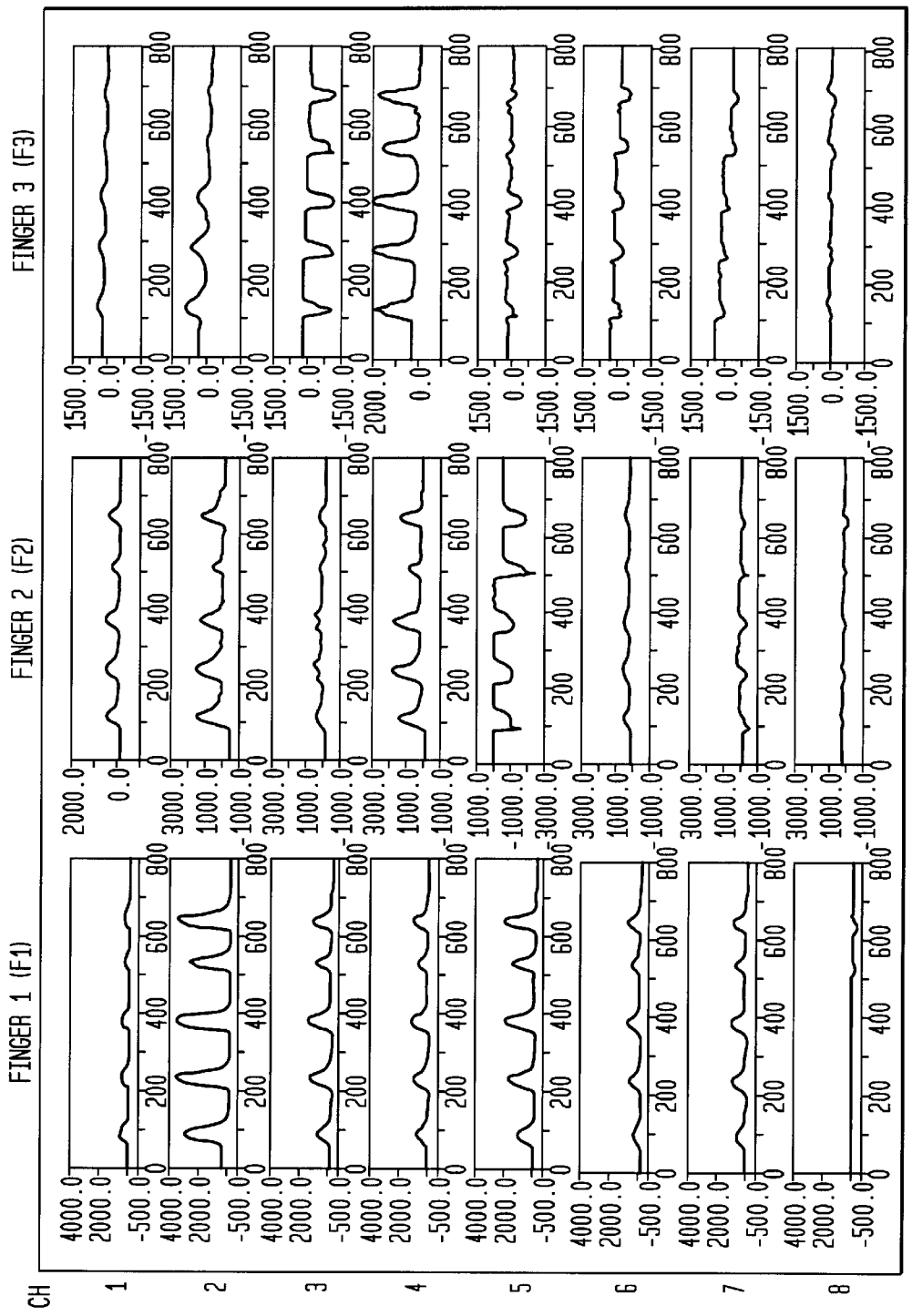
FIG. 4 shows training data representing 8 channels of data, acquired for three finger volitions: the thumb (F1), middle finger (F2) and pinky (F3). The ordinate is a relative amplitude scale, and the abscissa is sample number. Each signal trace represents 5 finger taps.
Figure 5A:
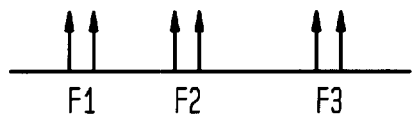
FIGS. 5A–5C show pressure vector decoding of myopneumatic (M-P) data.

The training protocol consisted of five full flexions of each of three fingers over a 4-second period (FIGS. 2, 4). The phantom fingers, F1, F2, and F3, represent the thumb, middle finger, and little finger, respectively. Test data were sequential double-flexions of each of the 3 fingers, during a 12-second period (FIGS. 5A, B). Output data were displayed in a response matrix consisting of three rows, representing the output used to control each phantom finger, and three columns, representing the requested finger motions (FIG. 5C). Diagonal components represent intended finger movements, while off-diagonal components represent the remaining effects of "movement cross-talk" occurring at the sensor locations. The goal of training was to maximize the signal on the diagonal, relative to the off-diagonal of the response matrix.

The system was trained and tested based on two types of signal features: the peak amplitude measure from each channel, and the RMS. The specificity of each feature extraction method was quantified as the ratios of the signal energies of the diagonal components over the off-diagonal components, for each finger movement sequence, according to:

$$R_{ij} = 10 \log \frac{\sqrt{\sum (D_i)^2}}{\sum (O_{ij})^2} \quad i, j = 1, 2, 3; i \neq j \quad (7)$$

where the numerator is the signal energy of the diagonal component on output channel i, and the denominator is the energy of the off-diagonal components, j, on channel i. Output channel records (FIG. 5C) were each segmented into three even segments prior to energy calculation, to separate the diagonal and off-diagonal components.

Results:

FIG. 4 shows 8 channels of intra-socket pressures recorded during supervised training of subject A. Records consist of 5 taps from each of 3 fingers. Upward signals represent positive pressure, due to outward movement at the M-P sensor site, while downward signals represent negative pressure due to inward movement (concavity). The amplitude of each signal thus indicates both the magnitude and sign of the mechanical deflection, whether it is a bulge or a concavity. Signal-to-noise ratio appears high for all channels except channel 8. Comparison of signals for each finger indicates that each movement produces a visibly different signal array, although some channels show more difference than others. For example, channels 3, 5, 6, and 7 record opposite polarities for F1 and F3, suggesting a reciprocal relationship whereby F1 causes a bulge and F3 causes a concavity at these sites. Channel 1, by contrast, appears to record similar amplitudes for all motions, indicating that the region near sensor 1 is commonly activated for all movements. Channel 8 has uniformly low amplitude, indicating it is in a mechanically inactive area.

To derive a filter based on the behavior of each channel during different movements, selected features of each signal are encoded by the feature matrix (3). For the filter shown in Table 1, signal features were represented by RMS values over the entire 5-tap sequence, producing the weights listed. As expected from the visual comparisons, and their low feature variances, weights for channels 1 and 8 were relatively low, representing their low discriminatory value.

TABLE 1

| | Features | | | | Weights | | |
|---|---|---|---|---|---|---|---|
| Ch | F1 | F2 | F3 | var | F1 | F2 | F3 |
| 1 | 1.85 | 1.98 | 0.98 | 0.3 | 0.05 | 0.18 | 0.00 |
| 2 | 13.84 | 5.45 | 3.66 | 29.5 | 0.53 | 0.32 | 0.01 |
| 3 | 4.91 | 1.86 | −4.42 | 22.6 | 0.28 | 0.46 | −0.89 |
| 4 | 3.60 | 5.37 | 7.42 | 3.7 | −0.02 | 0.22 | 0.77 |
| 5 | 7.05 | −7.33 | −1.48 | 52.3 | 0.46 | −1.00 | 0.11 |
| 6 | 2.86 | 1.30 | −2.29 | 7.0 | 0.16 | 0.28 | −0.48 |
| 7 | 3.19 | −1.84 | 3.50 | 9.0 | 0.12 | −0.51 | 0.61 |
| 8 | −0.47 | −0.46 | −0.61 | .01 | −0.01 | −0.02 | −0.06 |

Figure 5B:
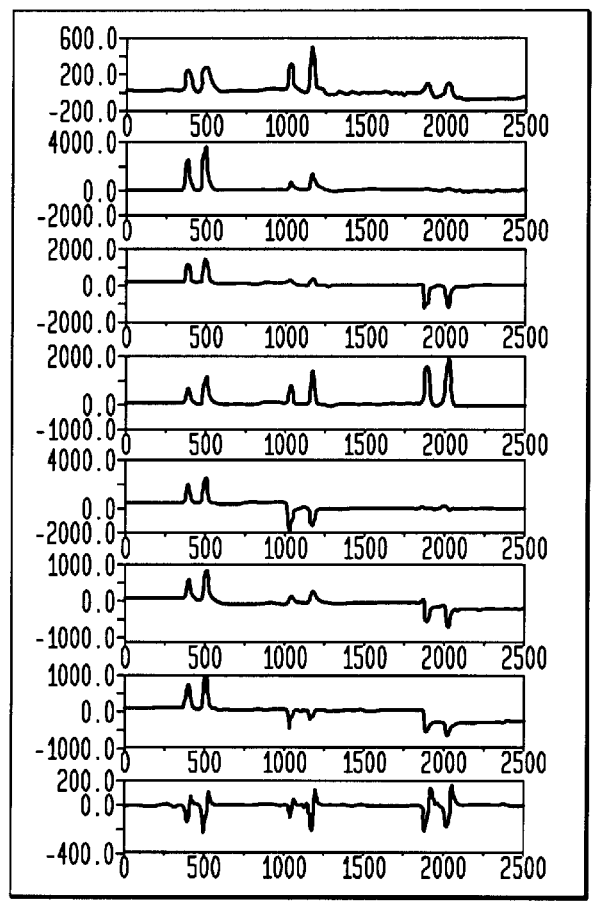
Figure 5C:
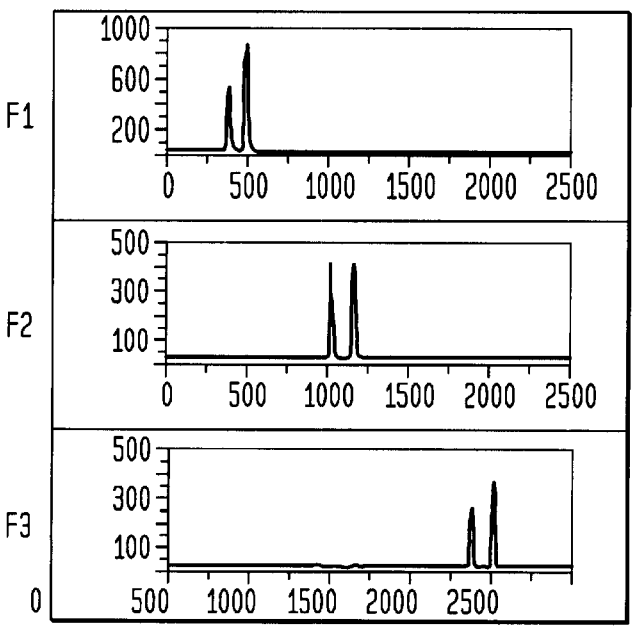

The filter derived above was tested by the Subject A (see FIG. 2, right branch), who voluntarily tapped each phantom finger twice in sequence, resulting in the raw input data shown in FIG. 5B (Note that scale differs from that of FIG. 4, ie. channel 8 is magnified by approximately an order of magnitude relative to FIG. 4). Complete specificity on any channel for a particular movement would be realized as a measurable signal for that finger (ie. F1), with zero signal amplitudes for the other two (ie: F2 & F3). Comparing finger movements for each channel, it is evident that channels 2 and 7 provide some degree of specificity for F1 movements, though some cross-talk exists on channel 2 with F2 (positively), and on channel 7 with both F2 and F3 (negatively). Little specificity is seen for F2 or F3 movements on any channel.

The filtered output (FIG. 5C) shows that all 6 movement requests were successfully decoded by the filter with a high degree of specificity, as seen by the large diagonal signals and near zero off-diagonal signals. Higher values represent greater specificity for volitional movements. It can be seen that near-complete specificity has been achieved, since the output control signals correspond with the intended volitional commands, found on the diagonal, with minimal signal content on the off-diagonal componets.

These relative magnitudes quantify the specificity of the filter using eq. (7), but are not necessarily related to volitional magnitude of movement. Although this filter is based on RMS features, the maximum-amplitude feature produced similar results (see Table 2 below), indicating that the two feature extraction methods have approximately equal discriminatory abilities for this subject. Referring to Table 2, values are given in dB, according to equation (7), calculated for Subject A, and represent the log signal energy of diagonals in relation to off-diagonal components. Overall score is represented by the sum.

As indicated in FIG. 2 (right), final decoding of discrete movement requests can be done by amplitude thresholding the output. Similar results were obtained from subject B.

TABLE 2

|  | PEAK Amplitude | RMS |
|---|---|---|
| $R_{12}$ | 7.8 | 10.0 |
| $R_{13}$ | 11.6 | 8.8 |
| $R_{21}$ | 9.7 | 5.4 |
| $R_{23}$ | 10.2 | 12.7 |
| $R_{31}$ | 10.9 | 11.9 |
| $R_{32}$ | 6.9 | 9.6 |
| Sum | 57.1 | 58.4 |

Values are shown in dB, according to equation (7), calculated for a single subject, and represent the log signal energy of diagonals in relation to off-diagonal components. Overall score is represented by the sum. It can be seen that near-complete specificity has been achieved, since the output control signals correspond with the intended volitional commands, found on the diagonal, with minimal signal content on the off-diagonal components.

Figure 6:
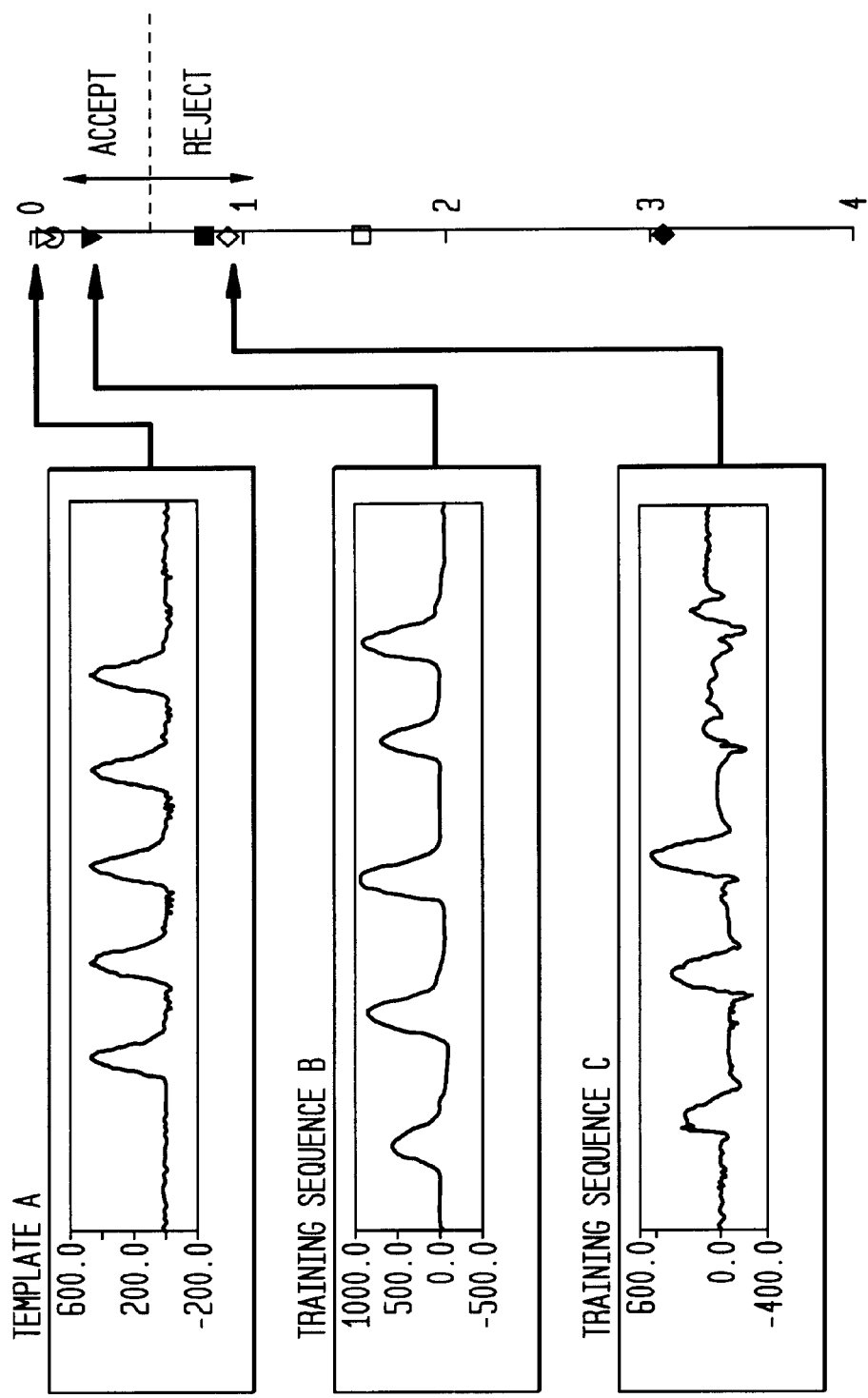
FIG. 6 shows cepstral distance evaluation of training data. As indicated on the plot, the template pattern 'A' represents zero Euclidean distance. Several training sequences are represented on the distance scale, denoted by the markers. The distances of training sequences 'B' and 'C', with respect to 'A', are also indicated. Distance is in cepstral units. Subthreshold distances indicate acceptable training sequences.

Evaluation of training data can be done using cepstral distances as shown in FIG. 6. Note that training sequence 1 (panel B) closely resembles the standard template (panel A), and is therefore valid, whereas sequence 2 (panel C) is distorted due to poor performance of either equipment or subject. A quantitative threshold criterion, based on Euclidean cepstral distance, can be applied to both sequences, resulting in acceptance of sequence 1, and rejection of sequence 2, as shown to the right.

Discussion:

The results suggest that specific motor commands can be decoded from the pressure vector exerted within the residual limbs of below-elbow amputees. To demonstrate this, a simple filter was trained to associate finger movement requests with pressures measured within the prosthetic socket, using M-P sensors. The filter is based on the pseudo-inverse of the feature matrix; somewhat analogous filtering techniques have been successfully applied to image processing Gonzalez, et al.; Shen, et al., "Filter-Based Coded Excitation System for High-Speed Ultrasonic Imaging," IEEE Trans. Med. Img., Vol. 17, No. 6, pp. 923–934, 1998, and audio source separation Kuo, et al., "Dual-Channel Audio Equalization and Cross Talk Cancellation for 3-D Sound Reproduction," IEEE Trans. Consumer Electronics, Vol. 43, No. 4, pp. 1189–1196, 1997. In limited testing of amputees under controlled conditions, the filter was easily trained and successfully controlled flexion of 3 phantom fingers.

Previous methods have been described to control prosthetic upper limbs using EMG signals from one or more sites on the upper body. Kang, et al.; Okuno, et al.; Chang, et al; Gallant, et al.; Park, et al. These methods can give the user control over basic limb movements, such as elbow flexion and wrist pronation, but have not controlled fingers. The difficulty in decoding joint movement requests from EMGs lies in the fact that they are asynchronous electrical pulses from many nerve and muscle fibers, whose mechanical resultant on individual motions is generally unpredictable. The Pressure Vector Decoding method is more suitable for dexterity control since the pressure vector is the final resultant of multiple motor pathways involved in specific joint movements.

The present study was limited to decoding specified movements, namely fixed-pattern tapping. For example, the output shown in FIG. 5C could actuate a pre-programmed tapping motion, but could not indicate its force or velocity, since these variables were not included in training. Preliminary evidence and previous results Abboudi et al; Phillips et al. have nevertheless suggested that, with proper sensor placement, degrees of proportional control can indeed be expressed by the PVD filter output. Implementing proportional control of either velocity or force may require additional training protocols that include graded magnitudes of volition. However, since a high degree of proportionality has been observed in tests, the use of the present filter method for proportional finger control is not ruled out.

It is also noted that the testing was done in a mostly static, unloaded arm position, and the robustness of the PVD method in real-life conditions remains unproven. The PVD method may perform relatively well in the presence of such interference, however, compared with EMG based methods. First, interfacial motion artifact due to sensor-skin sliding is small, since the M-P sensors are tightly apposed to the skin with a silicone sleeve, and no electrical noise is possible. Moreover, moisture-induced artifacts are eliminated. Secondly, static loading effects on the M-P signal are much less severe than on the EMG, which becomes continuously and globally contaminated with high frequency noise, whereas the pressure signals remain static. Thirdly, the simplicity of the PVD method facilitates its training under a variety of conditions. For example, distinguishing individual finger taps from various common motions such as wrist pronation and hand grasping can be done by the filter, since they have distinctive signal patterns [Abboudi, et al.] and training the filter to discriminate various motions is straightforward. Discrimination can be further optimized using systematic mechanical mapping of limb dynamics to determine optimal sensor sites [Phillips et al.].

B. Filter Training and Validity

The PVD filter is derived from the pseudoinverse of the M-P feature matrix that is trained by the user to recognize specific motions. The number of possible DOF depends upon the separability of the available training data, that is influenced not only by the technical performance of the sensing and decoding system, but also on the user's ability to produce distinctive pressure patterns within the socket for each movement. The users tested appear to have adequate ability [Abboudi, et al.], despite variable limb conditions and the presence of damaged tissues. Performance could no doubt be improved with practice and exercise, since residual muscles are subject to atrophy.

Since prostheses are removed daily, and limbs change constantly, the filter coefficients may require frequent re-training as sensors are re-aligned or as muscles change. Such re-training would require about 10 seconds per finger, and actual computation time for calculation of features and filter weights is less than 100 ms on a Pentium 400 MHz computer. Thus, re-calibration of the hand could be done conveniently as needed. During use (FIG. 2, right branch), the processing time for sensor-input data and generation of each output channel, as in equation (1), is 20 μs per sample. Real-time control of several prosthetic fingers using a mobile microcontroller thus appears possible.

Having thus described the invention in detail, it is to be understood that the foregoing description is not intended to limit the spirit and scope thereof. What is desired to be protected by Letters Patent is set forth in the appended claims.

What is claimed is:

1. A method for controlling digit movement on a prosthesis comprising:

interconnecting a plurality of mechanical sensors at locations on a forelimb;

acquiring data from the sensors during a training phase by flexing phantom digits while pressure signals are digitally sampled and stored;

filtering the data;

processing the data; and individually controlling digits of the prosthesis in accordance with the processed data.

2. The method of claim 1 wherein filtering is performed by an absolute peak method.

3. The method of claim 1 wherein filtering is performed by a root mean square method.

4. The method of claim 1 wherein training involves quantifying degradation of volitional commands through a limb sensor interface.

5. The method of claim 1 wherein training includes at least one full flexion of each digit over a short time period.

6. The method of claim 1 wherein the step of processing the data further comprises cepstral encoding the data.

7. The method of claim 1 wherein cepstral distance is used to validate training signal quality.

8. A method of training a filter for discriminating distributed pressures in a forelimb and controlling movements of digits on a prosthesis comprising:

positioning a plurality of sensors on a forelimb;

sampling pressure signals at the sensors on the forelimb corresponding to flexing of selected phantom digits; and extracting an amplitude feature for each sensor resulting in a feature vector for each digit of the prosthesis.

9. The method of claim 8 wherein the step of extracting the amplitude feature comprises using a peak amplitude method to determine a largest signal deviation.

10. The method of claim 8 wherein the step of extracting the amplitude feature comprises using a root mean square method.

11. The method of claim 8 wherein a feature matrix is formed from feature vectors for each digit.

12. The method of claim 11 wherein a pseudoinverse of the feature matrix is calculated.

* * * * *